United States Patent [19]

Cavero et al.

[11] Patent Number: 4,515,800
[45] Date of Patent: May 7, 1985

[54] METHOD OF LOWERING INTRAOCULAR PRESSURE USING PHENYLIMINO-IMIDAZOLES

[76] Inventors: Icilio Cavero, 8 rue Gabriel Fauré94000 Creteil; Salomón Z. Langer, 81, rue Jouffroy, 75017 Paris, both of France; Billie M. York, Jr., 3828 Winifred Dr., Fort Worth, Tex. 76153

[21] Appl. No.: 520,071

[22] Filed: Aug. 3, 1983

Related U.S. Application Data

[63] Continuation-in-part of Ser. No. 323,369, Nov. 20, 1981, abandoned.

[51] Int. Cl.$^3$ .............................................. A61K 31/415
[52] U.S. Cl. ..................................... 514/392; 514/913
[58] Field of Search ...................................... 424/273 R

[56] References Cited

U.S. PATENT DOCUMENTS

| | | | |
|---|---|---|---|
| 2,938,038 | 5/1960 | Hirt | 260/309.6 |
| 3,236,857 | 2/1966 | Zeik et al. | 260/309.6 |
| 3,468,887 | 9/1969 | Stahle et al. | 260/253 |
| 3,622,579 | 11/1971 | Stahle et al. | 424/273 |
| 3,636,219 | 1/1972 | Culik et al. | |
| 3,872,121 | 3/1975 | Kummer et al. | 424/273 |
| 3,931,216 | 1/1976 | Franymair | 260/309.6 |
| 4,125,620 | 11/1978 | Stahle et al. | 424/273 R |
| 4,166,859 | 9/1979 | Stahle et al. | 424/273 R |
| 4,213,995 | 7/1980 | Stahle et al. | 424/273 R |
| 4,250,186 | 2/1981 | Stahle et al. | 424/273 R |
| 4,262,005 | 4/1981 | McCarthy et al. | 424/273 R |
| 4,287,201 | 9/1981 | Olson et al. | |
| 4,293,564 | 10/1981 | Stahle et al. | 424/273 R |

FOREIGN PATENT DOCUMENTS

| | | |
|---|---|---|
| 2831657 | 2/1980 | Fed. Rep. of Germany . |
| 2832310 | 7/1980 | Fed. Rep. of Germany . |
| 2905883 | 8/1980 | Fed. Rep. of Germany . |
| 2947563 | 6/1981 | Fed. Rep. of Germany . |
| 2905345 | 7/1981 | Fed. Rep. of Germany . |
| 2949287 | 11/1981 | Fed. Rep. of Germany . |
| 35393 | 2/1981 | European Pat. Off. . |
| 43659 | 6/1981 | European Pat. Off. . |
| 792696 | of 1979 | South Africa . |
| 1180766 | 10/1967 | United Kingdom . |
| 1216945 | 12/1970 | United Kingdom . |
| 1279543 | 6/1972 | United Kingdom . |
| 1279931 | 6/1972 | United Kingdom . |
| 1595412 | 8/1981 | United Kingdom . |

OTHER PUBLICATIONS

J. Pharmcol. Methods 6(2) 109-20 (1981)—Stahle et al.
J. Labelled Compd. Radiopharm 17(1) 35-41 (1980)—Rouot et al.
J. Med. Chem. 24 502-507 (1981)—Pieter et al.
Naunyn-Schmiedeberg's Arch Pharmacol 317(8)-12 (1881) DeJonge et al.
J. Anton. Pharmac. 1, 377-383 (1981) DeJonge et al.
Brit J. Pharmac. 71, 5-9 (1980) Roust et al.
Cr Acad. Sci. Pares 286 (1978)—Rouot et al.
Life Science 25, 769-774 (1979)—Rouot et al.
Invent. Ophthal 17(2)—149-158 Krieglotein et al."The Peripheral & Central Neural Action of Clonidine".
Chem. Abst. 92, 41,944(d) & 41946(f)—Stalhe et al. (1980).
"The Effect of Selective $\alpha_1$—and $\alpha_2$—Adrenocepter Stimulation on Intraocular Pressure in the Conscious Rabbit" by Innemee et al in Naunyn-Schmiedeberg's Arch Pharmacol (1981) 316, 294-298.
∫Electroencephalographic Studies on Clonidine and Para-Amino-clonidine, a Potent Peripherally Acting Imidazoline" by Depoortere et al. in Sleep (1980) pp. 297-800.
37 Pharmacological Studies on Para-Aminoclonidine" by Cavero et al. in British Journal of Pharmacology (1980) 69, 295P-296P.
"Synthese et reactivite de la p-aminochlonidine" by Rouot et al. in Bulletin de la Societe Chimique de France at (1979) 79 (9-10) pt2:502-528.

*Primary Examiner*—Douglas W. Robinson
*Attorney, Agent, or Firm*—Fitch, Even, Tabin & Flannery

[57] ABSTRACT

A method is provided of treating glaucoma in a patient which comprises administering, preferably as eye drops, an effective amount of the compound

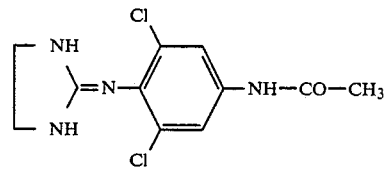

which is preferably in the form of its hydrochloride. The compound is administered preferably in the form of a sterile pharmacologically acceptable solution which contains from 0.1 to 5, and more preferably 0.1 to 2.0, percent by weight of said compound. The patient preferably obtains the anti-glaucoma agent in the form of a kit which comprises the sterile pharmacologically acceptable solution and an eyedropper for dispensing said sterile pharmacologically acceptable solution to the affected eyes of a patient suffering from glaucoma.

3 Claims, No Drawings

METHOD OF LOWERING INTRAOCULAR PRESSURE USING PHENYLIMINO-IMIDAZOLES

This is a continuation-in-part application of U.S. Ser. No. 323,369 filed Nov. 20, 1981, now abandoned.

This invention relates to the treatment of glaucoma and ocular hypertension with α-adrenergics. More particularly, this invention relates to a method of lowering intraocular pressure (hereinafter "IOP") by the topical administration to the eye of an effective amount of particular 2-(trisubstituted phenylimino)-imidazoline compounds, also known as 2-(trisubstituted-anilino)-1,3-diazacyclopentene-(2) compounds.

In glaucoma and ocular hypertension, the high pressure within the affected eye presses against the blood vessels nourishing the optic nerve head and retina. When these blood vessels collapse under abnormal ocular pressure, an atrophy of specific regions of the retina results which ultimately is related to loss of vision and blindness. It is known that certain α-adrenergics, such as clonidine, also known as 2-(2',6'-dichloroanilino)-1,3-diazacyclopentene-(2) and under the naming and indexing of chemical substances for Chemical Abstracts as 2,6-dichloro-N-(2-imidazolidinylidene)-benzamine, are capable of lowering IOP. However, these compounds affect the central nervous system and lower systemic blood pressure, cause drowsiness and other undesirable side effects.

Unexpectedly, it has been discovered that the compounds of the invention exert a selective and local ocular pharmacological action which lowers IOP without lowering systemic blood pressure. When the compounds of the invention are applied topically to the eye they do not have to cross the blood barrier of the brain to effect IOP lowering. These compounds lower IOP through a local or peripheral α-adrenergic action at dose levels which selectively lower IOP without significantly affecting the central nervous system.

The IOP lowering action of the compounds of the invention is unexpected because the locus of clonidine action has been deemed in the art to be primarily mediated by the brain. The compounds of the invention surprisingly have been found to be excluded from significant absorption into the central nervous system or brain when administered topically at concentrations required to lower ocular IOP. Unexpectedly, therefore, it has been found that the compounds of the invention exert a potent IOP lowering by a local action without significantly lowering systemic blood pressure or causing other central nervous system side effects such as drowsiness.

It has been found that the following compounds, or pharmaceutically acceptable acid salts thereof, will selectively lower IOP at dosage levels which do not significantly lower systemic blood pressure:

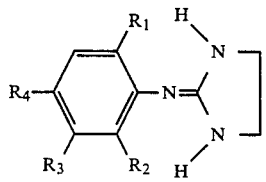

I. $R_1 = R_2$ = methyl, ethyl, trifluoromethyl, chloro or bromo, $R_1 \neq R_2$ and each = methyl, ethyl, trifluoromethyl, fluoro, chloro or bromo, one of $R_3$ and $R_4$ is H and the other is selected from

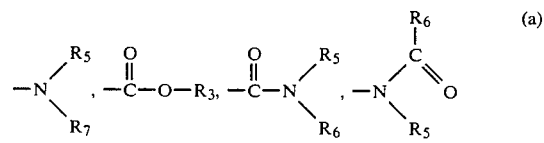

(a)

$R_5 = R_6$ = H or lower alkyl, $R_5 \neq R_6$ and each = H, lower alkyl, $R_7$ = H, lower alkyl 2-hydroxyethyl, 2-hydroxypropyl or 3-hydroxypropyl, the sum of the carbon atoms in $R_5$ and $R_6$ or $R_5$ and $R_7$ being 4 or less or

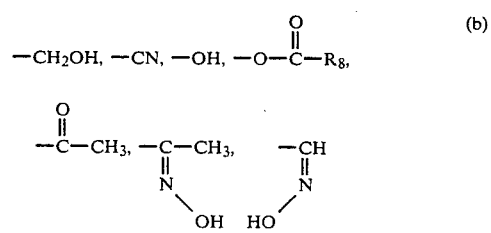

(b)

$R_8$ = lower alkyl;

II. $R_1$—methyl, ethyl, trifluoromethyl, chloro or bromo, $R_2$ = H, $R_3$ is selected from

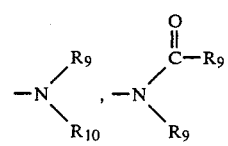

$R_4$ = methyl, chloro or bromo $R_9$ = H or lower alkyl, $R_{10}$ = H, lower alkyl, 2-hydroxymethyl, 2-hydroxypropyl or 3-hydroxypropyl, the sum of the carbon atoms in $R_9$ and $R_{10}$ being 4 or less.

The alkyl substituents may be straight or branched chain. Generally methyl and ethyl derivatives are prepared because they do not easily enter the central nervous system relative to larger alkyl groups.

The compounds in the form of the free base or a salt such as the hydrochloride or dihydrochloride preferably are formulated as aqueous eye drops having a concentration of the compounds of the invention in the range of 0.10 to 2.0 percent by weight. The amount of the eye drops will vary depending upon the concentration of the compounds of the invention. Buffering agents, disinfectants and preservatives may be added as is known in the art.

Examples of the compounds of the invention were made as follows in accordance with the following examples.

EXAMPLE I

N-[3,5-Dichloro-4-(2-imidazolidinylideneamino)-phenyl]-formamide Free Base

N-[3,5-Dichloro-4-(2-imidazolidinylideneamino)-phenyl]-formamide which structurally is

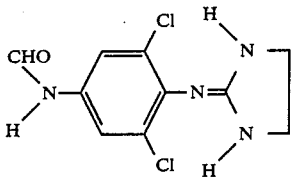

may be made by the following procedure.

Formic acid (35 mL, 98%) and acetic anhydride (15 mL) are stirred and heated at 50° C. for 30 minutes then cooled to 10° C. Then 2,6-dichloro-$N^1$-(2-imidazolidinylideneamino)-1,4-benzenediamine dihydrochloride (12 g.) is added in portions. The mixture then is heated to 50° C. for 5 hours and then stirred for 6 hours at ambient temperature. Ether (50 mL) is added to the stirred mixture and colorless solids are collected by filtration with ether washes (100 mL) to yield after drying 12.2 g. of product with a melting point of 241°–242° C. with decomposition and a mass spectral analysis of $m/e^+272$ for $C_{10}H_{10}Cl_2N_4O$. The free base is prepared by treatment of the product with 1N sodium hydroxide with prompt extraction by ethyl acetate. The dried ethyl acetate extract is dried over anhydrous sodium sulfate and evaporated to yield a white powder (10.1 g).

EXAMPLE II 2,6-Diethyl-N-(2-imidazolidinylidene)-benzamine Free Base 2,6-Diethyl-N-(2-imidazolidinylidene)-benzamine Free Base which structurally is

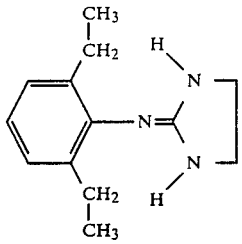

may be made by the following procedure.

1. 1-Acetyl-2-imidazoline may be prepared from 2-imidazoline as follows:

2-Imidazoline (60 g., 0.7 mol) is suspended in acetic anhydride (500 mL) and the mixture is heated to reflux for 30 minutes, then is reduced in volume with heat and reduced pressure to a wet solid. Ethanol (250 mL) is added and a colorless solid collected by filtration. The solid is air dried to yield crude 1-acetyl-2-imidazoline (60.5 g.) having a melting point of 176°–180° C. (literature melting point of 176°–177° C. as reported in *J. Chem. Soc.* 176 (1964).

2. 2,6-Diethyl-N-(2-imidazolidinylidene)-benzamine may be prepared from 1-acetyl-2-imidazoline as follows:

1-Acetyl-2-imidazoline (12.6 g., 0.11 mol) in phosphorus oxychloride (140 mL) is stirred and heated to 45° C.; then 2,5-diethylbenzamine (16.5 mL, 0.10 mol) is added at a rate to maintain 50° C. After 24 hours the phosphorus oxychloride is evaporated with heat and reduced pressure. The resultant amber syrup then is poured onto ice (700 cc). The pH is adjusted to 12 with sodium hydroxide, and the aqueous mixture is extracted with methylene chloride (3×75 mL). The combined extracts then are washed with a sodium hydroxide solution (50 mL) and water (2×50 mL) and dried over magnesium sulfate. Evaporation of the methylene chloride results in a solid which is triturated with petroleum ether (30°–60° C. boiling range, 250 mL) and collected by filtration (11.6 g., m.p. 134°–137° C.). Recrystallization from cyclohexane yields 2,6-diethyl-N-(2-imidazolidinylidene)-benzamine, (7.0 g., m.p. 138°–139° C.). Elemental analysis of the product shows it has the following composition: calculated for $C_{15}H_{21}N_3O$: C 69.46%, H 8.16%, N 16.20%; observed C 69.39%, H 8.25%, N 16.27%.

3. As the final step in the synthesis, 2,6-diethyl-N-(2-imidazolidinylidene)-benzamine may be prepared from 2,6-diethyl-N-[1-acetyl-(2-imidazolidinylidene)]-benzamine as follows:

2,6-Diethyl-N-[1-acetyl-(2-imidazolidinylidene)]-benzamine (4.0 g., 15.4 mmol) is suspended in water (125 mL) and then is heated to reflux. After 3.5 hours the resulting clear colorless solution is cooled, ice is added, and the pH adjusted to 13 with sodium hydroxide. A white precipitate forms and is collected by filtration, is washed with water (80 mL) and then dried to yield 2,6-diethyl-N-(2-imidazolidinylidene)-benzamine free base white powder (3.1 g. 93%) with a melting point of 155°–157° C. and a mass spectral analysis of $m/e^+\cdot 217$ for $C_{13}H_{19}N_3$.

EXAMPLE III 2,6-Diethyl-$N^1$-(2-imidazolidinylidene)-1,4 benzenediamine Dihydrochloride 2,6-Diethyl-$N^1$-(2-imidazolidinylidene)-1,4-benzenediamine dihydrochloride which structurally is

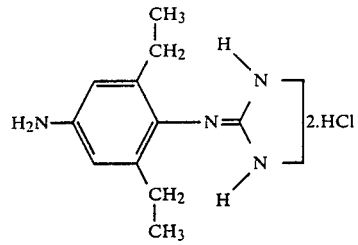

may be made by the following procedure.

1. 2,6-Diethyl-4-nitro-N-(2-imidazolidinylidene)-benzamine may be prepared from 2,6-diethyl-N-(2-imidazolidinylidene)-benzamine (from EXAMPLE II) as follows:

2,6-Diethyl-N-(2-imidazolidinylidene)-benzamine (4.35 g., 20 mmol) is added to a solution of fuming nitric acid (4.5 mL) in water at 5° C. Acetic acid (20 mL) then is added to the latter solution. Sodium nitrite (310 mg., 4.5 mmol) then is added to the latter mixture and the reaction is heated to reflux. After two hours, the reaction is cooled to room temperature and additional sodium nitrite (310 mg.) in water (4 mL) is added. After four additional hours at reflux the mixture is stirred overnight at room temperature. The reaction mixture is poured onto ice, the pH was adjusted to 13, and a yellow precipitate is collected by filtration and air dried (4.5 g.). Column chromatography (silica gel; ethyl acetate, acetone, triethylamine (98:1.5:0.5)) yields 2,6-diethyl-4-nitro-N-(2-imidazolidinylidene)-benzamine which is triturated after drying with petroleum ether, filtered, air dried (0.95 g.) and has a mass spectral analysis of m/e+·262 for C$_{13}$H$_{18}$N$_4$O$_2$.

2. As the final step in the synthesis: 2,6-diethyl N$^1$-(2-imidazolidinylidene)-1,4-benzenediamine dihydrochloride may be prepared from 2,6-diethyl-4-nitro-N-(2-imidazolidinylidene)-benzamine as follows:

2,6-Diethyl-4-nitro-N-(2-imidazolidinylidene)-benzamine (750 mL) is dissolved in ethanol (80 mL). Ethanol washed Raney Nickel (700 mg.) then is added and the yellow mixture treated with hydrogen gas (45 psi) overnight to yield a colorless filtrate. The colorless filtrate is evaporated to an oil which forms needles upon standing, the needles having a mass spectral analysis of m/e+·232 for C$_{13}$H$_{20}$N$_4$. This solid is then dissolved in methanol (50 mL), cooled to 5° C. and hydrogen chloride gas is bubbled through. After 45 minutes the solution is evaporated to yield an oil which when treated with ethyl ether gives 2,6-diethyl-N$^1$-(2-imidazolidinylidene)-1,4-benzenediamine dihydrochloride which is a colorless powder (0.72 g.) having a melting point with decomposition of 250° C. Elemental analysis for the dihydrochloride salt shows it has the following composition: calculated for C$_{13}$H$_{22}$Cl$_2$N$_4$: C 51.15%, H 7.26%, N 18.35%; observed: C 50.83%, H 7.25%, N 18.09%.

EXAMPLE IV

N-[3,5-Diethyl-4-(2-imidazolidinylideneamino)-phenyl]-acetamide Hydrochloride

N-[3,5-Diethyl-4-(2-imidazolidinylideneamino)-phenyl]-acetamide hydrochloride which structurally is

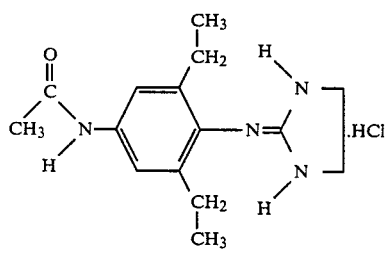

may be made by the following procedure.

2,6-Diethyl-N$^1$-(2-imidazolidinylidene)-1,4-benzenediamine dihydrochloride (1.9 g., 6.2 mmol), the synthesis of which is shown in EXAMPLE III, is suspended in acetic acid (15 mL) and stirred at room temperature for 20 minutes. A solution of acetyl chloride (1.35 mL, 18.6 mmol) in acetic acid (4 mL) is added dropwise to the latter suspension over 15 minutes at ambient temperature. After the addition is complete, the temperature is raised to 50° C. for 5 hours with stirring and then is cooled.

Upon cooling, the reaction mixture is poured onto ice and the pH is adjusted to 13. The resulting solid is extracted into ethyl acetate (100 mL) which is evaporated. The resulting residue is triturated with acetonitrile, is filtered and dried (1.23 g.). The resulting solid is dissolved in chloroform, is treated with charcoal, and filtered through celite. Evaporation of the chloroformer under reduced pressure and heat yields a solid form. This solid then is dissolved in methanol and treated with hydrogen chloride gas at 15° C. and after 45 minutes is precipitated with ether. Recrystallization from a methanol and ether combination yields a sample of about 1.1 g. of N-[3,5-diethyl-4-(2-imidazolidinylideneamino)-phenyl]-acetamide hydrochloride having a melting point of 267° C. and a mass spectral analysis of m/e+·274 for C$_{15}$H$_{22}$N$_4$O.

EXAMPLE V 3,5-Dichloro-4-(2-imidazolidinylideneamino)-benzenecarboxamide 3,5-Dichloro-4-(2-imidazolidinylideneamino)-benzenecarboxamide which structurally is

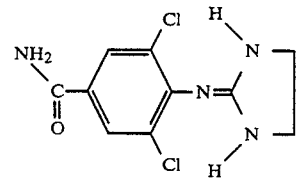

may be made by the following procedures.

Into a three-necked 500 mL round-bottomed flask equipped with a mechanical stirrer, reflux condenser, and thermometer and charged with 4-cyano-2,6-dichlorobenzamine (4 g., 0.016 m) in 30 mL of absolute ethanol is added hydrogen peroxide (9 mL of 30% in 81 mL of water) and potassium hydroxide (4.52 g. of 30% solution). The reaction mixture is heated to a temperature of 45° C. over a thirty-minute period and maintained at this temperature for two additional hours. At this time, the solution is cooled to 0° C. with an ice bath and filtered to yield 1.8 g. of whitish crystalline material. Subsequent reduction in volume of the filtrate results in an additonal 1.1 g. of the same material coming out of solution for a crude yield of 2.9 g. or 68% of theoretical. Recrystallization from water/ethanol solvent leads to a light yellow powder which has a melting point of 243°-245° C. and gives the expected IR with double absorption in the 1700 to 1640 cm$^{-1}$ region.

Elemental analysis for the salt shows it has the following composition: calculated for C$_{10}$H$_{10}$N$_4$Cl$_2$: C 43.98%, H 3.69%, N 20.51%, Cl 25.96%; observed: C 43.82%, H 3.79%, N 20.39%, Cl 26.08%.

Alternatively, this example and other N- and N,N-disubstituted carboxamides can be prepared according to the German Offenlegungsschrift No. 2,905,883, Aug. 28, 1980.

EXAMPLE VI 2,6-Diethyl-N$^1$-(2-imidazolidinylidene)-1,3-benzenediamine Dihydrochloride 2,6-Diethyl-N$^1$-(2-imidazolidinylidene)-1,3-benzenediamine dihydrochloride which structurally is

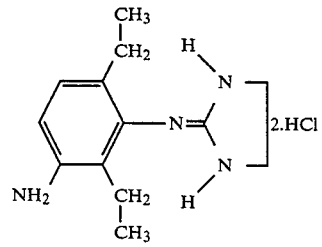

may be made by the following procedure.

1. 2,6-Diethyl-3-nitro-N-(2-imidazolidinylidene)-benezenamine may be prepared from 2,6-diethyl-N-(2-imidazolidinylidene)-benzamine as follows:

Sulfuric acid (20 mL) is cooled to 5° C. and 2,6-diethyl-N-(2-imidazolidinylidene)-benzamine (2.17 g., 10 mmol) is added with rapid stirring. After the solid dissolves to give a dark solution, a mixture of concentrated nitric acid (0.75 mL, 12 mmol) and sulfuric acid (1.0 mL) is slowly added at 0°–5° C. Upon complete addition, the reaction is stirred at 0°–5° C. for one hour and then is poured onto ice (150 mL) and filtered. The filtrate is basified with sodium hydroxide (pH 13) and then is extracted with ethyl acetate (3×100 mL). Chromatography (silica gel; ethyl acetate, acetone, triethylamine (92:2.5:0.5) yields a sample (1.5 g.) with a melting point of 131°–133° C. and a mass spectral analysis of m/e+·262 for $C_{13}H_{18}N_4O_2$.

2. 2,6-Diethyl-$N^1$-(2-imidazolidinylidene)-1,3-benzenediamine dihydrochloride may be prepared from 2,6-diethyl-3-nitro-N-(2-imidazolidinylidene)-benzamine as follows:

2,6-Diethyl-3-nitro-N-(2-imidazolidinylidene)-benzamine (1 g., 3.8 mmol) is dissolved in ethanol (80 mL) and Raney Nickel (1 g.) in ethanol (10 mL) is added. The latter solution then is treated with hydrogen (45 psi) for 15 hours. The resulting almost colorless solution is filtered and evaporated to a foam which then is dissolved in methanol (50 mL), treated with charcoal and filtered. The filtrate is cooled to 5° C. and hydrochloride gas is passed through the solution for ½ hour. The concentrated solution is treated with ethyl acetate and the resulting solid is collected by filtration. Elemental analysis of the salt shows that it has the following composition: calculated for $C_{13}H_{20}N_42HCl$: C 51.15%, H 7.26%, N 18.35%; observed: C 51.06%, H 7.36%, N 18.34%.

EXAMPLE VII 2,6-Dichloro-$N^1$-(2-imidazolidinylidene)-1,3-benzenediamine Hydrochloride 2,6-Dichloro-$N^1$-(2-imidazolidinylidene)-1,3-benzenediamine hyrochloride which structurally is

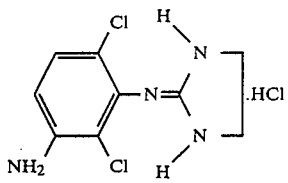

may be made by the following procedure.

1. 2,6-Dichloro-3-nitro-N-(2-imidazolidinylidene)-benzamine is prepared as follows:

2,6-Dichloro-N-(2-imidazolidinylidene)-benzamine or clonidine is prepared according to the procedure of R. Rouot et al., *J. Med. Chem.*, 19, 1049–54 (1976). Clonidine (11.45 g., 50 mmol) is suspended with stirring in cold sulfuric acid (30 mL). Then a solution of 70% nitric acid (50 mL, 55 mmol) and concentrated sulfuric acid (50 mL) is added dropwise with stirring over a period of thirty minutes. The reaction is stirred for two additional hours at 5°–10° C. and then poured into ice (500 cc) with stirring forming a yellow solution. Sodium hydroxide pellets (28 g.) then are added to the yellow solution. Then 5% sodium hydroxide solution is added to the solution until the pH is approximately 3.

Then the pH adjusted solution is extracted with ethyl acetate (5×500 mL). The combined ethyl acetate extracts then are dried over anhydrous sodium sulfate and then are filtered through celite. The filtrate is evaporated with heat and reduced pressure to yield a solid yellow foam which is triturated with hexanes and collected by filtration to yield a product (10.2 g.) with a melting point of 154°–156.5° C. High resolution mass spectroscopy analysis for $C_9H_8Cl_2N_4O_2$: calculated 274.0024, observed 274.0020, error 0.4 mmu/1.5 ppm. 2. 2,6-Dichloro-$N^1$-(2-imidazolininylidene)-1,3-benzebenzenediamine hydrochloride may be made from 2,6-dichloro-nitro-N-(2-imidazolininylidene)-benamine as follows:

To a mechanically stirred suspension of 2,6-dichloro-3-nitro-N-(2-imidazolidinylidene)-benzamine (5 g., 18 mmol), iron powder (3.1 g., 56 mmol) and ethanol (50 mL) at reflux is added dropwise a solution of concentrated hydrochloric acid (4.6 mL) in 60% ethanol (25 mL). After the addition, the reaction is refluxed for one hour with stirring. Then potassium hydroxide (3N, 17.6 mL) is added while stirring. After the latter addition, the mixture is filtered while hot through a celite pad. The filtrate then is evaporated with heat and reduced pressure. The residue is dissolved in hot methanol treated with activated charcoal and is refiltered through a celite pad. Again the solvent is evaporated leaving an off-white solid (4.1 g.) with a melting point of 263°–266° C. with decomposition. High resolution mass spectroscopy analysis for $C_9H_{10}Cl_2N_4$: calculated 244.0282, observed 244.0291, error 0.9 mmu/3.7 ppm.

German Offenlegunsggshrift No. 2,806,811 of Staehle et al., Aug. 23, 1979, *Chemical Abstracts* 92: 41944d, illustrates the following compounds:

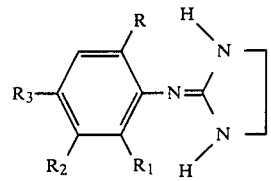

where:
1. R=$R_3$=Cl or Br, $R_2$=NH$_2$, $R_1$=H
2. R=$R_3$=Cl or Br, $R_2$=H, $R_1$=NH$_2$
3. R=$R_3$=Me, $R_2$=NH$_2$, $R_1$=H
4. R=$R_3$=Me, $R_2$=H, $R_1$=NH$_2$
5. R=Cl or Br, $R_3$=Me, $R_2$, $R_1$=H
6. R=Cl or Br, $R_3$=H, $R_2$=NH$_2$, $R_1$=H
7. R=Cl or Br, $R_3$=H, $R_2$=H, $R_1$=NH$_2$
8. R=H, $R_3$=Cl or Br, $R_2$=H, $R_1$=NH$_2$
9. R=$R_3$=Cl or Br, $R_2$=CH$_2$OH, $R_1$=H
10. R=$R_3$=Cl or Br, $R_2$=H, $R_1$=CH$_2$OH
11. R=H, $R_3$=Cl or Br, $R_2$=CH$_3$, $R_1$=NH$_2$
12. R=Cl or Br, $R_3$=F, $R_2$=NH$_2$, $R_1$=H
13. R=Cl or Br, $R_3$=Cl or Br, $R_3$=NH$_2$, $R_1$=F
14. R=Cl or Br, $R_3$=F, $R_2$=H, $R_1$=NH$_2$
15. R=F, $R_3$=Cl or Br, $R_2$=H, $R_1$=NH$_2$ Further, in any compound having the above structure discussed in German Offenlegungsschrift No. 2,806,811, the amine of the benzene ring of such compound may have the following constituents including alkyl analogues or amides:

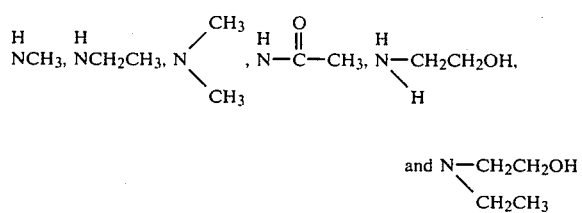

In an article entitled "Synthese et reactive de la p-aminochlonidine" by Rouot et al. in Bulletin de la Societe Chimique de France at 79 (9-10) pt 2: 205-528 (1979) the following components were disclosed

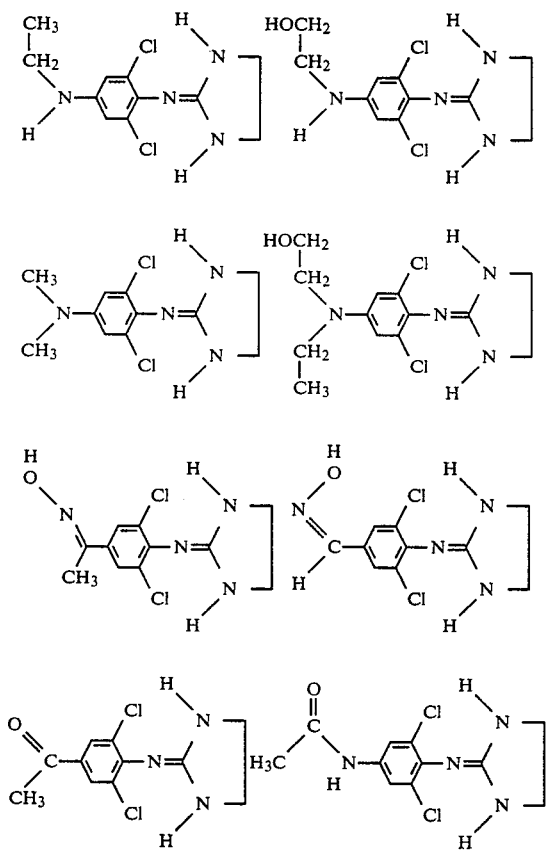

U.S. Pat. No. 4,094,964 to Jarrott et al. discloses the following compound:

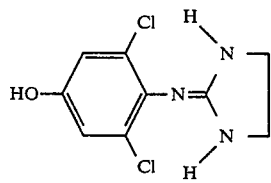

German Offenlegungsschrift No. 2,805,775 of Stahle et al., Aug. 30, 1979, Chemical Abstracts 92: 41946f illustrates the following compounds:

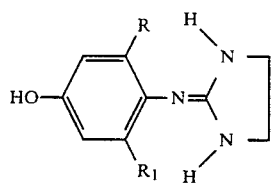

where
R=R$_1$=Br
R=Cl, R$_1$=Br
R=Cl, R$_1$=Me or lower alkyl, preferably methyl or ethyl.

EXAMPLE VIII 2,6-Dichloro-N$^1$-(2-imidazolidinylidene)-1,4-benzenediamine Dihydrochloride 2,6-Dichloro-N$^1$-(2,imidazolidinylidene-1,4-benzenediamine Dihydrochloride which structurally is

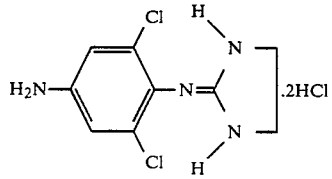

may be made by the following procedure.

1. 2,6-Dichloro-1,4-benezenediamine is prepared as follows:

Wet Raney Nickel (50 g., ethanol washed) is added to 2,6-dichloro-4-nitroaniline (100 g., 9.48 mol, Aldrich Chemical Co.) in ethanol (800 mL) in a glass-lined pressure vessel which is charged with hydrogen (50 psi) for six hours while the reaction mixture is mechanically stirred. After the reaction and the hydrogen gas is evacuated, the reaction mixture is filtered through a celite pad, evaporated to a small volume and poured into one liter of water. The resulting solid is collected on a filter and air dried to yield 112 grams of 2,6-dichloro-1,4-benezenediamine having a melting point of 118°–120° C. (literature melting point of 124°–125° C.). 2. N-(4-Amino-3,5-dichlorophenyl)-trichloroacetamide may be prepared from 2,6-dichloro-1,4-benzenediamine as follows:

2,6-Dichloro-1,4-benzenediamine (225 g., 1.27 mol) is suspended in methylene chloride (1.3 liters) containing triethylamine (245 mL, 1.7 mol). After the mixture is cooled to 5° C., trichloroacetylchloride (169 mL, 1.5 mol, Aldrich Chemical Co.) is added dropwise with stirring at a rate to maintain 5° C. Upon complete addition, the stirred reaction is allowed to reach room temperature. After 24 hours the mixture is filtered and the collected solid is washed with methylene chloride (700 mL). The filtrate is evaporated to a small volume. A solid is collected and washed with methylene chloride (250 mL) to yield 465 grams of N-(4-amino-3,5-dichlorophenyl)-trichloroacetamide. The product exhibits a mass spectral analysis of m/e$^+$·320 for C$_8$H$_5$Cl$_5$N$_2$O. 3. N-(3,5-Dichloro-4-formamidophenyl)-trichloroacetamide may be prepared from N-(4-amino-3,5-dichlorophenyl)-trichloroacetamide as follows:

Acetic anhydride (600 mL, 6.4 mol) and 90% formic acid (275 mL, 5.4 mol) are heated to reflux for 45 minutes and then cooled to 5° C. The N-(4-aminon-3,5- dichlorophenyl)-trichloroacetamide (464 g., 1.44 mol) is added to the mixed anhydride solution and mechanically stirred for 20 hours at room temperature. Then the reaction mixture is poured onto ice (2 liters). When the stirred slurry reaches room temperature, it is collected by suction filtration and washed with water (1.5 liters) and dried to constant weight yielding 348.7 grams of N-(3,5-dichloro-4-formamidophenyl)-trichloroacetamide with a mass spectral analysis of m/e+·348 for $C_9H_5Cl_5N_2O_2$.

4. N-(3,5-Dichloro-4-dichloromethaniminophenyl)-trichloroacetamide may be prepared from N-(3,5-dichloro-4-formamidophenyl)-trichloroacetamide as follows:

To N-(4-amino-3,5-dichloro-4-formamidophenyl-trichloroacetamide (200 g., 0.57 mol) in thionyl chloride (415 mL, 3.5 mol) at reflux is dropwise added sulfuryl chloride (92 mL, 1.0 mol) over a 7-hour period. The reaction is heated for an additional 30 minutes and then allowed to stir at room temperature overnight. The reaction mixture then is reduced in volume by distillation in vacuo. The cooled solid is dissolved in ethyl acetate (200 mL), is treated with activated charcoal (4 g.), and is filtered through a celite pad followed with an ethyl acetate wash. The filtrate is evaporated to dryness with heat and reduced pressure. The solid N-(3,5-dichloro-4-dichloromethaniminophenyl)-trichloroacetamide is triturated with hexanes (600 mL), filtered and dried (164.8 g., 0.41 mol). A second crop of crystalline product may be collected from the mother liquor (29.72 g.). The product exhibits a mass spectral analysis of m/e+·400 for $C_9H_3Cl_7N_2O$.

5. N-[3,5-Dichloro-4-(2-imidazolidinylideneamino)-phenyl]-trichloroacetamide hydrochloride may be made from N-(3,5-dichloro-4-dichloromethaniminophenyl)-trichloroacetamide as follows:

To triethylamine (300 mL) in ethyl acetate (500 mL), mechanically stirred is dropwise added simultaneously N-(3,5-dichloro-4-dichloromethaniminophenyl)-trichloroacetamide (163 g., 0.4 mol) in ethyl acetate (225 mL) and ethylenediamine (40 mL, 0.74 mol) in ethyl acetate (350 mL). The addition of the former is accomplished in 5 hours, the latter in 7 hours. The temperature during the addition ranges from 29°–33° C. The resulting suspension is stirred for another 15 hours at ambient temperature. The suspension is filtered with ethyl acetate wash (200 mL) and the combined filtrates are evaporated with heat and reduced pressure. Then toluene (200 mL) is added and the product is evaporated to dryness. A solid forms and is dissolved in ethyl acetate (800 mL) which then is cooled to 0° C. Hydrogen chloride gas is bubbled into the solution at less than 10° C. A white solid precipitate is collected by filtration, washed with ethyl acetate (200 mL) and dried to yield N-[3,5-dichloro-4-(2-imidazolidinylideneamino)-phenyl]-trichloroacetamide hydrochloride (180 g.) with a mass spectral analysis of m/e+·388 for $C_{11}H_9N_4Cl_5O$.

6. As the final step in the synthesis, 2,6-dichloro-$N^1$-(imidazolidinylideneamino)-1,4-benzenediamine dihydrochloride may be prepared from N-[3,5-dichloro-4-(2-imidazolidinylideneamino)-phenyl]-trichloroacetamide hydrochloride as follows:

To a solution of N-[3,5-dichloro-4-(2-imidazolidinylideneamino)-phenyl]-trichloroacetamide hydrochloride (262.5 g.) in methanol (750 mL) is added methanol saturated with anhydrous ammonia (750 mL). The solution is stirred at room temperature for four days under anhydrous conditions. The solution then is evaporated to dryness and the crystalline product triturated with ethyl ether (4×400mL). The crystals are collected and dried to yield 137.5 g. of product. The crystals then are dissolved in methanol (1.8 liters), the solution is cooled to 10° C. and hydrogen chloride gas then is passed through the stirred solution at such a rate as to maintain the temperature below 15° C. After an hour a solid is collected and washed with cold methanol. Reprecipitation from methanol/ether and drying yields the dihydrochloride salt as a colorless or white powder (124.6 g.). Elemental analysis of the product shows that it has the following composition: calculated for $C_9H_{12}Cl_4N_4$: C 33.94%, H 3.80%, N 17.62%; observed: C 33.79%, H 4.00%; N 17.44%.

EXAMPLE IX 3,5-Dichloro-4-(2-imidazolidinylideneamino)-benzoic acid ethyl ester 3,5-Dichloro-4-(2-imidazolidinylideneamino)-benzoic acid ethyl ester which structurally is

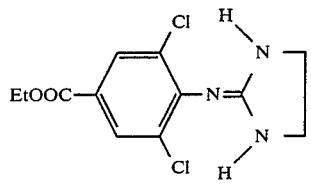

may be made by the following procedure.

1. Preparation of 4-amino-3,5-dichlorobenzoic acid ethyl ester:

Reaction of 4-aminobenzoic acid ethyl ester (20.7 g., 0.125 m. Aldrich Chem. Co.) with 430 mL of 6N HCl and 30% $H_2O_2$ (25.3 mL, 0.25 m) leads to the formation of 27.1 g. of reddish brown crystalline solid with a melting point of 46°–49.5° C.

2. 3,5-Dichloro-4-(2-imidazolidinylideneamino)-benzoic acid ethyl ester may be made from 4-amino-3,5-dichlorobenzoic acid ethyl ester as follows:

Following the procedure in Rouot et al., in *J. Med. Chem.*, 19, 1049 (1976), 4-amino-3,5-dichlorobenzoic acid ethyl ester (70.2 g., 030 m) is reacted with the product from acetic anhydride (61.3 g., 0.60 m) and formic acid (34.5 g., 0.75 m) to yield the desired 3,5-dichloro-4-formamidobenzoic acid ethyl ester (62.0 g., 0.237 m) in crude yield of 79% with a melting point of 168°–170° C. Reaction of this crude (16.35 g., 0.062 m) with a mixture of thionyl chloride (55.4 g., 0.47 m) and a sulfuryl chloride (3.4 g., 0.062 m) leads to the desired 3,5-dichloro-4-dichloromethaniminobenzoic acid ethyl ester (14.65 g., 46 mmol) which distills at 105° C. at 250 mm of Hg after standard workup. It should be noted that this material may solidify on standing. Finally, this distilled dichloromethamine (4.35 g., 0.0138 m) is reacted with ethylene diamine (1.66 g., 0.0276 m), and 10 mL of triethylamine in approximately 25 mL of ethyl acetate for 10 hours. An immediate white precipitate is noted, but stirring is continued overnight to ensure complete reaction. This reaction mixture then is vacuum filtered to yield 5.35 g. of white powder (which is greater than 100% yield, but is probably due to the fact that, in addition to the desired compound, triethylamine hydrochloride as well as the hydrochloride of the desired compound are present at this stage). Recrystallization of the white powder from absolute ethanol produced a white crystalline solid (2.3 g., 0.0076 m) in a yield of 55% with a melting point of 238°–240° C. This compound demonstrates the expected IR absorptions at 3380 (sharp), 3150 (broad), 1710 (sharp), 1660 (sharp and most intense), 1580 (sharp), 1275 (sharp), 1105 cm$^{-1}$ (sharp).

Elemental analysis of the product shows that it has the following composition: calculated for $C_{12}H_{13}N_3Cl_2O_2$: C 47.70%, H 4.34%, N 13.91%, Cl 23.47%; observed: C 47.66%; H 4.41%; N 13.88%; Cl 23.82%.

EXAMPLE X 3,5-Dichloro-4-(2-imidazolidinylideneamino)-benzenemethanol

This compound is structurally

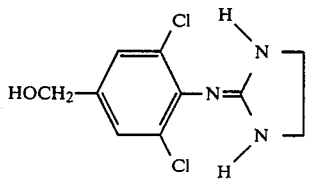

and may be made by the following.

This compound is synthesized by direct reduction of the corresponding ester of EXAMPLE IX, or the compound also can be prepared according to Stahle, Koeppe, Kummer, Holfke and Pichler, Boehringer C. H. Sohn Ger. Offen. No. 2,806,811 Aug. 23, 1979. Thus, 3,5-dichloro-4-(2-imidazolidinylideneamino)-benzoic acid ethyl ester (3.03 g., 0.01 m) is dissolved in 70 ml of dry benzene in a three-necked 250 mL round-bottomed flask equipped with nitrogen inlet, magnetic stirrer, addition funnel, reflux condenser, and thermometer. Twelve ml of a 24% solution of diisobutyl aluminum hydride (3.0 g., 0.021 m) in toluene is added over 30 minutes and the mixture heated for an additional 2-hour period while maintaining the temperature at 45° C. Standard work up leads to 1.6 g (61%) of yellowish crystalline material with a melting point of 195°–200° C. Subsequent recrystallization from absolute ethanol led to an almost white crystalline material with a melting point of 212°–214° C. The IR spectrum of this compound was consistent with the desired compound.

Elemental analysis of the product shows that it has the following composition: calculated for $C_{10}H_{11}N_3Cl_2O$: C 46.17%, H 4.26%, N 16.15%, Cl 27.26%; observed: C 46.11%, H 4.27%, N 16.13%, Cl 27.48%.

EXAMPLE XI 3,5-Dichloro-4-(2-imidazolidinylideneamino)-benzoic acid

This compound is structurally

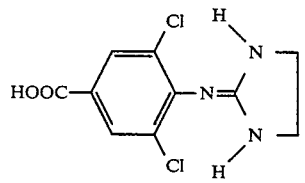

and may be made by the following procedure.

This compound is synthesized by acid hydrolysis of the corresponding ester of EXAMPLE IX. Thus, a solution of 3,5-dichloro-4-(2-imidazolidinylideneamino)-benzoic acid ethyl ester (4.5 g., 0.015 m) in 10 mL of 6N HCl is added to 150 ml of 10% HCl at a temperature of 70° C. in a 250 mL three-necked round-bottomed flask equipped with a reflux condenser and magnetic stirrer. The resulting solution was heated to reflux for 1.5 hours, cooled to cause precipitation, and vacuum filtered to yield 4.0 g. (86%) of a crude white powder, which did not melt below 320° C. Recrystallization of this material from absolute ethanol led to a white powder which did not melt below 320° C. and which had an IR spectrum consistent with the title compound.

Anal. Calcd. for $C_{10}H_{10}N_3Cl_3O_2$: C, 38.67%; H, 3.25%; N, 13.53%; Cl, 34.25%. Found: C, 38.78% H, 3.30%; N, 13.42%; Cl, 34.10%.

EXAMPLE XII

4-Cyano-2,6-dichloro-N-(2-imidazolidinylidene)-benzamine Hydrochloride

This compound is structurally

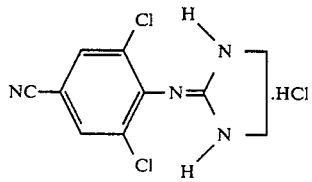

and may be made by the following procedure.

1. Preparation of 4-cyano-2,6-dichlorobenzamine.

Reaction of 4-cyanobenzamine (10 g., 0.085 m, Aldrich Chem. Co.) with 292 ml of 6N HCl and 30% $H_2O_2$ (17.2 mL, 0.17 m) led to the formation of a white crystalline compound with a melting point of 113°–115° C. The yield of this compound was 12.3 g.

2. 4-Cyano-2,6-dichloro-N-(2-imidazolidinylidene)-benzamine may be prepared from 4-cyano-2,6-dichlorobenzamine as follows:

4Cyano-2,6-dichlorobenzamine (8.00 g., 0.043 m) is converted to the corresponding N-(4-cyano-2,6-dichlorophenyl)-formamide (7.05 g., 0.033 m) for a 77% yield of a white powder with a melting point of 198°–200° C. Treatment of this formamide (4.3 g., 0.020 m) with thionyl chloride (35.7 g., 0.30 m) and sulfuryl chloride (4.10 g., 0.03 m) yields N-(4-cyano-2,6-dichlorophenyl)-dichloromethanimine (3.9 g., 0.0145 m) which is obtained by distillation at 110° C. at 250 mmHg for a yield of 73%. The product, which solidifies readily after the solvent and reactants have been completely stripped from the reaction mixture, is washed with hexanes. The dichloromethanimine (3.0 g., 0.011 m) is reacted with ethylene diamine and leads to the title compound (2.3 g., 0.0089 m ) as a yellow white powder in a crude yield of 81% with a melting point of 245°–250° C. Subsequent recrystallization from absolute ethanol leads to fluffy, cream-colored needles having a melting point of 255°–258° C. The IR spectrum of this compound was consistent with the title compound with prominent absorption at 2200 and 1650 cm$^{-1}$.

Elemental analysis of the product shows that it has the following composition: calculated for $C_{10}H_8N_4Cl_2$: C 47.08%, H 3.16%, N 21.96%, Cl 27.79%; observed: C 46.93%, H 3.32%, N 21.71%, Cl 27.88%.

EXAMPLE XIII

6-Chloro-$N^1$-(2-imidazolidinylidene)-4-methyl-1,3-benzenediamine Dihydrochloride 6-Chloro-$N^1$-(2-imidazolidinylidene)-4-methyl-1,3-benzenediamine dihydrochloride which structurally is

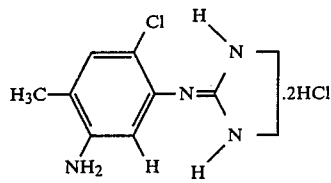

may be made by the following procedure.

1. Preparation of N-(2-chloro-4-methylphenyl)-formamide is as follows:

Acetic anhydride (50 mL, 0.53 mol) and 97–100% formic acid (21.5 mL, 0.45 mol) are reacted to 50° C. for 15–20 minutes with stirring whereupon the solution is cooled to 0° C. 2-chloro-4-methylbenzamine (35.3 g., 30.7 mL, 0.25 mol, Aldrich Chem. Co.) then is added dropwise over 15 minutes with stirring. Then the stirred solution is heated to 50° C. for 7 hours. The solution is evaporated to dryness with heat and reduced pressure and the residue recrystallized from toluene (150 mL) to yield colorless crystals.

2. N-(2-Chloro-4-methylphenyl)-dichloromethanimine may be prepared from N-(2-chloro-4-methylphenyl)-formamide as follows:

To N-(2-chloro-4-methylphenyl)-formamide (15.0 g., 88 mmol) in thionyl chloride (78.5 g., 48 mL, 0.66 mmol) is added dropwise sulfuryl chloride (11.9 g., 7.1 mL, 88 mmol). The stirred solution is heated for 9 hours with a dry ice condenser affixed. Then the reaction solution is concentrated by heat and reduced pressure. Distillation (55°–65° C. at 100 mm Hg) yields a product (16.0 g.).

3. 6-Chloro-N-(2-imidazolidinylidene)-4-methyl benzamine may be prepared from N-(2-chloro-4-methylphenyl)-dichloromethanimine as follows:

To triethylamine (55 mL) in ethyl acetate (40 mL) mechanically stirred is dropwise added simultaneously N-(2-chloro-4-methylphenyl)-dichloromethanimine (16 g., 72 mmol) in ethyl acetate (20 mL) and ethylenediamine (8.6 g., 9.6 mL, 144 mmol) in ethyl acetate (20 mL) over a period of 50 minutes. The reaction mixture is allowed to stir for an additional 20 hours at ambient temperature. The mixture is filtered and the filtrate is evaporated with heat and reduced pressure. The residue is triturated with ethyl acetate and collected by filtration and air dried (4.2 g.). The layer chromatography on silica gel (chloroform, methanol, concentrated ammonium hydroxide: 8.5, 1.5., 2 drops) showed the product at Rf=0.5. The product exhibits a mass spectral analysis of m/e+·209 for $C_{10}ClH_{12}N_3$.

4. 6-Chloro-N-(2-imidazolidinylidene)-4-methyl-2-nitro-benzamine may be made from 6-chloro-N-(2-imidazolidinylidene)-4-methyl-benzamine as follows:

To 6-chloro-N-(2-imidazolidinylidene)-4-methyl-benzamine (1.0 g., 4.8 mmol) in concentrated sulfuric acid (5 mL) at 5° C. is added dropwise with stirring to a solution of concentrated sulfuric acid (0.26 mL) and 70% nitric acid (0.33 mL) during a 15 minute period. After thirty minutes the darkened reaction mixture is poured onto ice, basified to pH 10 with ammonium hydroxide and extracted with ethyl acetate (4×50 mL). The combined extracts are dried over anhydrous sodium sulfate. Evaporation with heat and reduced pressure yields a yellow powder (1.1 g.). Recrystallization from toluene yields a yellow solid (0.4 g.) which gives a single spot on thin layer chromatography with silica gel (chloroform, methanol, concentrate ammonium hydroxide: 9, 1, 2 drops) Rf=0.73. The product exhibits a mass spectral analysis of m/e+·254 for $C_{10}H_{11}ClN_4O_2$.

5. 6-chloro-$N^1$-(2-imidazolidinylidene)-4-methyl-1,3-benzenediamine dihydrochloride may be made from 6-chloro-N-(2-imidazolidinylidene)-4-methyl-3-nitrobenzamine as follows:

To a mechanically stirred suspension of 6-chloro-N-(2-imidazolidinylidene)-4-methyl-3-nitrobenzamine (0.5 g., 2 mmol), iron powder (0.65 g., 6 mmol) and 50% ethanol (10 mL) is added dropwise hydrochloric acid (1.0 mL). The reaction mixture then is refluxed for one hour and then sodium hydroxide is added. The reaction mixture is filtered and the solid washed with ethanol. The filtrate is evaporated to dryness, dissolved in methanol and filtered. The filtrate is evaporated again, redissolved in methanol (30 mL) and hydrogen chloride gas is bubbled through the solution. After evaporation the solid is titrated with ether (3×30 mL) yielding a product after recrystallization from methanol (0.25 g.) with a melting point of 243°–248° C. with decomposition. The product exhibits a mass spectral analysis of m/e+·224 for $C_{10}H_{13}ClN_4$. Elemental analysis of the product shows: $C_{12}H_{15}Cl_2N_4$. ½ $H_2O$: calculated C 39.17%, H 5.26%, N 18.27%; observed: C 38.79%, H 5.09%, N 17.95%.

EXAMPLE XIV 2,6-Dichloro-$N^1$-(2-imidazolidinylidene)-$N^4$, $N^4$-dimethyl-1,4-benzenediamine Dihydrochloride 2,6-Dichloro-$N^1$-(2-imidazolidinylidene)-$N^4$, $N^4$-dimethyl-1,4-benzenediamine dihydrochloride which structurally is

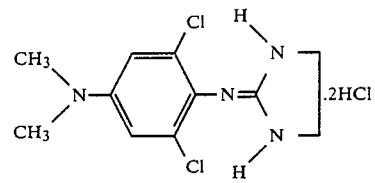

may be made by the following procedure.

2,6-dichloro-N-¹-(2-imidazolidinylidene)-$N^4$, $N^4$-dimethyl-1,4-benzenediamine dihydrochloride was prepared according to the general procedure of R. Rouot and G. Leclerc, *Bull. Soc. Chim. Fr.*, 1979 (pt. 2), 520–28 with the exception that the free base was converted to the dihydrochloride salt. The free base of 2,6-dichloro-$N^1$-(2-imidazolidinylidene)-$N^4$,$N^4$-dimethyl-1,4-benzenediamine (0.5 g.) after chromatographic purification was dissolved in methanol (40 mL) and cooled to 5°–10° C. in an ice bath and hydrogen chloride gas was bubbled through the solution. The solution was treated with powdered charcoal (1 g.), filtered through a celite pad, evaporated to dryness and triturated with ether to yield a white powder (1.7 g.) with a melting point of 275°–277° C. with decomposition. NMR (CDCl₃, TMS): 2.85 (amine methyls, 6H, S), 3.50 (ethylene; 4H, S) 6.67 (aromatic, 2H, S). Mass spectral analysis m/e+·272 for $C_{11}H_{14}Cl_2N_4$.

In addition to the examples set forth herein, compounds contemplated for use in the present invention include the following free bases and pharmaceutically acceptable salts:

2,6-Dibromo-N$^1$-(2-imidazolidinylidene)-1,4-benzenediamine;
2,6-Dibromo-N$^1$-(2-imidazolidinylidene)-1,3-benzenediamine;
N-[3,5-Dibromo-4-(2-imidazolidylideneamino)-phenyl]-acetamide;
N-[2,4-Dibromo-3-(2-imidazolidinylideneamino)-phenyl]-acetamide;
3,5-Dibromo-4-(2-imidazolidinylideneamino)-phenol and phenolic esters thereof;
2,6-Ditrifluoromethyl-N$^1$-(2-imidazolidinylidene)-1,4-benzenediamine;
2,6-Ditrifluoromethyl-N$^1$-(2-imidazolidinylidene)-1,3-benzenediamine;
N-[3,5-Ditrifluoromethyl-4-(2-imidazolidinylideneamino)-phenyl]-acetamide;
2,6-Dimethyl-N$^1$-(2-imidazolidinylidene)-1,4-benzenediamine;
2,6-Dimethyl-N$^1$-(2-imidazolidinylidene)-1,3-benzenediamine;
N-[3,5-Dimethyl-4-(2-imidazolidinylideneamino)-phenyl]-acetamide;
N-[2,4-Dimethyl-3-(2-imidazolidinylideneamino)-phenyl]-acetamide;
N-[2,4-Diethyl-3-(2-imidazolidinylideneamino)-phenyl]-acetamide;
3,5-Dimethyl-4-(2-imidazolidinylideneamino)-phenol and phenolic esters thereof;
3,5-Diethyl-4-(2-imidazolidinylideneamino)-phenol and phenolic esters thereof;
3,5-Dibromo-4-(2-imidazolidinylideneamino)-phenol and phenolic esters thereof;
2,6-Dichloro-N$^1$-(2-imidazolidinylidene)-N$^4$-methyl-1,4-benzenediamine;
2,6-Dibromo-N$^1$-(2-imidazolidinylidene)-N$^4$-methyl-1,4-benzenediamine;
2,6-Dimethyl-N$^1$-(2-imidazolidinylidene)-N$^4$-methyl-1,4-benzenediamine;
2,6-Diethyl-N$^1$-(2-imidazolidinylidene)-N$^4$-methyl-1,4-benzenediamine;
2,6-Dibromo-N$^4$, N$^4$-dimethyl-N$^1$-(2-imidazolidinylidene)-1,4-benzenediamine;
2,6-Dimethyl-N$^4$, N$^4$-dimethyl-N$^1$-(2-imidazolidinylidene)-1,4-benzenediamine;
2,6-Diethyl-N$^4$, N$^4$-dimethyl-N$^1$-(2-imidazolidinylidene)-1,4-benzenediamine;
N$^4$, N$^4$-Dimethyl-N$^1$-(2-imidazolidinylidene)-2,6-ditrifluoromethyl-1,4-benzenediamine;
N-[3,5-Dichloro-4-(2-imidazolidinylideneamino)-phenyl]-N-methyl-acetamide;
N-[3,5-Dibromo-4-(2-imidazolidinylideneamino)-phenyl]-N-methyl-acetamide;
N-[3,5-Diethyl-4-(2-imidazolidinylideneamino)-phenyl[-N-methyl-acetamide;
3,5-Dichloro-4-(2-imidazolidinylideneamino)-benezenemethanol and esters thereof;
N-[3-bromo-5-chloro-4-(2-imidazolidinylideneamino)-phenyl]-acetamide;
N-[3-bromo-5-chloro-4-(2-imidazolidinylideneamino)-phenyl]-N-methyl-acetamide;
3-Bromo-5-chloro-4-(2-imidazolidinylideneamino)-phenol and phenolic esters thereof;
3,5-Dibromo-4-(2-imidazolidinylideneamino)-benzenecarboxamide;
3,5-Dichloro-4-(2-imidazolidinylideneamino)-benzene-N,N-dimethyl-carboxamide;
3,5-Dibromo-4-(2-imidazolidinylideneamino)-benzoic acid and alcohol esters thereof;
3,5-Dibromo-4-(2-imidazolidinylideneamino)-benezenemethanol and esters thereof.

Other compounds contemplated by the invention are:
A. 3,5-Dichloro-4-(2-imidazolidinylideneamino)-benzoic acid ethyl ester;
B. 3-Chloro-5-ethyl-4-(2-imidazolidinylideneamino)-benzoic acid ethyl ester;
C. 3,5-Diethyl-4-(2-imidazolidinylideneamino)-benzoic acid ethyl ester;
D. N-[3-chloro-5-ethyl-4-(2-imidazolidinylideneamino)-phenyl]-acetamide;
E. 2-chloro-6-ethyl-N$^1$-(2-imidzolidinylidene)-1,4-benzenediamine;

and pharmaceutically acceptable salts thereof.

The efficacy of several 2-(trisubstituted anilino)-1,3 diazacyclopentene-(2) compounds shown in Table I in lowering IOP without affecting the central nervous system using clonidine as a control was tested by the following biological procedures. (A to E).

The data from the hereinafter described tests is illustrated in Table I.

A. RHESUS MONKEY—LASER MODEL

Ocular hypertension was produced in adult Rhesus monkeys (4) via an argon laser photocoagulation of trabecular meshwork in the eye. The treated eye (only one is lasered) was allowed to heal and the IOP stabilized after about six weeks. Tests were performed by topical administration of one drop of a 0.5% solution of the test agent to the Ketamine anesthetized Rhesus monkey's eye. The IOP charge was recorded by an Alcon Applanation Phneumatonograph. The peak effect was recorded as a percentage change in the hypertensioned eye versus the IOP value of the same eye recorded at the same hour the previous day.

B. NORMAL RABBIT MODEL

To determine the IOP reduction efficacy of the anti-glaucoma drugs of the invention in normal albino rabbitts the following was done.

New Zealand albino rabbits (12) were acclimatized in restraining boxes for thirty minutes. Alcaine/saline (1:5) was applied to the rabbit eyes and baseline IOP in mm Hg pressure were measured using an Alcon Laboratory Applanation Phneumatonograph. Then thirty minutes later, the coded test substance versus a coded saline control was administered as a 50 ul drop to one eye, six animals in each group. The treatment effects were measured as a function of time. Mean IOP and mean change in IOP for each hourly reading was recorded. The effect cited is a peak percentage effect versus the external control test group.

C. The "STEROID" RABBIT MODEL

Biological procedures for measuring IOP effects of drugs in the "steroid" rabbit model are given in B. L. Bonomi and L. Tomayzol, *Invest. Ophthal.* 15, 781,784 (1976) and L. Bonomi et al., *Albrect Graefes Arch. Ophthal.*, 209, 73, 89. Luciano Bonomi et al., *Albrect Graefes Arch. Ophthal.*, 219, 1, 8, (1979) shows the model works for known anti-glaucoma drugs. In the experiments shown in Table I, a drop of the drug was administered to one eye of the subject rabbit and the IOP in the treated eye was monitored as a function of time.

D. 20% BLOOD PRESSURE DECREASE IN THE RAT

Six Sprague-Dawley rats (6 per test group at 200–400 g.) are anesthetized (65 mg/kg sodium pentobarbital) and placed on a heating pad. The femoral artery was cannulated and hydrolically connected to a pressure transducer and Grass Model 7 recorder. A fifteen minute blood pressure reading was recorded. A buffered test agent was given intravenously in a small volume (i.e., 0.1 mL). The test agent effect on blood pressure was then recorded. The mean dose calculated to lower blood pressure 20% in the rat is given in ug/kg.

E. POTENTIATION OF HEXOBARBITAL INDUCED ANESTHESIA

Concomitant intraparateneal administration of the test drug and hexobarbital to mice will result in an increase in the duration of anesthesia as compared to hexobarbital alone, if the test compound has sedative activity. This potentiation can be used as a relative measure of central nervous system effect (sedative activity) for comparison of test compounds. The endpoint of anesthesia was recorded as the recovery of the "righting reflex".

TABLE I

IOP Lowering Data
(Drop In Intraocular Pressure After Topical Administration Of Drug)

| | (A) 50 uL 0.5% topical Laser-Monkey % IOP | (B) 50 uL 1% topical Normal Rabbit % IOP |
|---|---|---|
| $R_1 = R_2 = Cl$; $R_3 = R_4 = H$ 2,6-Dichloro-N—(2-imidazolidinylidene)-benezamine Free Base | −32.0% | −13.9% |
| $R_1 = R_2 = Cl$; $R_3 = H, R_4 = NH_2$ 2,6-Dichloro-$N^1$—(2-imidazolidinylidene)-1,4-benzenediamine Dihydrochloride | −21.0% | −1.3% |
| $R_1 = R_2 = Cl$; $R_3 = H, R_4 = NCOH$ N—[3,5-Dichloro-4-(2-imidazolidinylideneamino)-phenyl]-formamide Free Base | −26.0% | −15.6% |
| $R_1 = R_2 = Cl$; $R_3 = H, R_4 = NCOCH_3$ N—[3,5-Dichloro-4-(2-imidazolidinylideneamino)-phenyl]-acetamide Hydrochloride | −4.0% | −19.0% |
| $R_1 = R_2 = Cl$; $R_3 = H, R_4 = -OH$ 3,5-Dichloro-4-(2-imidazolidinylideneamino)-phenol Hydrochloride | −23.0% | −7.4% |
| $R_1 = R_2 = Cl$; $R_3 = -NH_2, R_4 = H$ 2,6-Dichloro-$N^1$—(2-imidazolidinylidene)-1,3-benzenediamine Hydrochloride | — | 0.0% |
| $R_1 = R_2 = Cl$; $R_3 = H, R_4 = -CH_2-OH$ 3,5-Dichloro-4-(2-imidazolidinylideneamino)-benzenemethanol Hydrochloride | −17% | 0.0% |
| $R_1 = R_2 = Cl$; $R_3 = H, R_4 = COOH$ 3,5-Dichloro-4-(2-imidazolidinylidene amino)-benzoic Acid | — | −4.5% |
| $R_1 = R_2 = Cl$; $R_3 = H, R_4 = CO_2C_2H_5$ 3,5-Dichloro-4-(2-imidazolidinylideneamino)-benzoic Acid Ethyl Ester | — | −5.6% |
| $R_1 = R_2 = Cl$; $R_3 = H, R_4 = N(CH_3)_2$ 2,6-Dichloro-$N^1$—(2-imidazolidinylidene)-$N^4,N^4$-dimethyl-1,4-benzenediamine Dihydrochloride | — | −10.2% |
| $R_1 = R_2 =$ ethyl; $R_3 = H, R_4 = H$ 2,6-Diethyl-N—(2-imidazolidinylidene)-benzamine Free Base | — | — |
| $R_1 = R_2 =$ ethyl; $R_3 = H, R_4 = NH_2$ 2,6-Diethyl-$N^1$—(2-imidazolidinylidene)-1,4-benzenediamine Dihydrochloride | — | — |
| $R_1 = R_2 =$ ethyl; $R_3 = H, R_4 = -NCOCH_3$ N—[2,6-Diethyl-4-(2-imidazolidinylideneamino)-phehyl]-acetamide Hydrochloride | — | — |
| $R_1 = R_2 =$ ethyl; $R_3 = -NH_2, R_4 = H$ 2,6-Diethyl-$N^1$—(2-imidazolidinylidene)-1,3-benzenediamine Dihydrochloride | — | — |
| $R_1 = R_2 = Cl$; $R_3 = H, R_4 = -CN$ 4-Cyano-2,6-dichloro-N—(2-imidazolidinylidene)-benzamine | — | −2.3% |
| $R_1 = R_2 = Cl$; $R_3 = H, R_4 = -CONH_2$ 3,5-Dichloro-4-(2-imidazolidinylideneamino)-benzenecarboxamide Free Base | — | — |
| $R_1 = Cl; R_2 = H; R_3 = NH_2; R_4 = CH_3$ 6-Chloro-$N^1 =$ (2-imidazolidinylidene)-4-methyl-1,3-benzenediamine Dihydrochloride | | |

| | (C) 50 uL 0.5% topical Steroid Rabbit % IOP | (D) Dose 50 ul/kg 20% b.p. Decease Rat |
|---|---|---|
| $R_1 = R_2 = Cl$; $R_3 = R_4 = H$ 2,6-Dichloro-N—(2-imidazolidinylidene)-benezamine Free Base | −27.0% | 4.8 |
| $R_1 = R_2 = Cl$; $R_3 = H, R_4 = NH_2$ 2,6-Dichloro-$N^1$—(2-imidazolidinylidene)-1,4-benzenediamine Dihydrochloride | −25.0% −25.0%[2] −21.0%[3] | 50.0 |
| $R_1 = R_2 = Cl$; $R_3 = H, R_4 = NCOH$ N—[3,5-Dichloro-4-(2-imidazolidinylideneamino)-phenyl]-formamide Free Base | −30.0% | 30.0 |
| $R_1 = R_2 = Cl$; $R_3 = H, R_4 = NCOCH_3$ | −30.0% | 18.0 |

TABLE I-continued
IOP Lowering Data
(Drop In Intraocular Pressure
After Topical Administration Of Drug)

| Compound | (E) Dose 50 uL/kg | (F) IOP[1] |
|---|---|---|
| N—[3,5-Dichloro-4-(2-imidazolidinylideneamino)-phenyl]-acetamide Hydrochloride $R_1 = R_2 = Cl$; $R_3 = H, R_4 = -OH$ | −4.0% | 38.0 |
| 3,5-Dichloro-4-(2-imidazolidinylideneamino)-phenol Hydrochloride $R_1 = R_2 = Cl$; $R_3 = -NH_2, R_4 = H$ | −25.0% | 16.0 |
| 2,6-Dichloro-$N^1$—(2-imidazolidinylidene)-1,3-benzenediamine Hydrochloride $R_1 = R_2 = Cl$; $R_3 = H, R_4 = -CH_2, -OH$ | −26.0% | 190.0 |
| 3,5-Dichloro-4-(2-imidazolidinylideneamino)-benzenemethanol Hydrochloride $R_1 = R_2 = Cl$ $R_3 = H, R_4 = COOH$ | −19.9% | 50,000.0 |
| 3,5-Dichloro-4-(2-imidazolidinylideneamino)-benzoic Acid $R_1 = R_2 = Cl$; $R_3 = H, R_4 = CO_2C_2H_5$ | −20.7% −14.0[3] | 27,000.0 |
| 3,5-Dichloro-4-(2-imidazolidinylideneamino)-benzoic Acid Ethyl Ester $R_1 = R_2 = Cl$; $R_3 = H, R_4 = N(CH_3)_2$ | — | 1,000.0 |
| 3,6-Dichloro-$N^1$—2-imidazolidinylidene)-$N^4,N^4$-dimethyl-1,4-benzenediamine Dihydrochloride $R_1 = R_2 = $ ethyl; $R_3 = H, R_4 = H$ | 11.3% | 19.0 |
| 2,6-Diethyl-N—(2-imidazolidinylidene)-benzamine Free Base $R_1 = R_2 = $ ethyl; $R_3 = H, R_4 = NH_2$ | — | 10.0 |
| 2,6-Diethyl-$N^1$—(2-imidazolidinylidene)-1,4-benzenediamine Dihydrochloride $R_1 = R_2 = $ ethyl; $R_3 = H, R_4 = -NCOCH_3$ | — | 130.0 |
| N—[2-6-Diethyl-4-(20 imidazolidinylideneamino)-phenyl]-acetamide Hydrochloride $R_1 = R_2 = $ ethyl; $R_3 = -NH_2, R_4 = H$ | — | 100.0 |
| 2,6-Diethyl-$N^1$—(2-imidazolidinylidene)-1,3-benzenediamine Dihydrochloride $R_1 = R_2 = Cl$; $R_3 = H, R_4 = -CN$ | — | 8,300.0 |
| 4-Cyano-2,6-dichloro-N—(2-imidazolidinylidene)-benzamine $R_1 = R_2 = Cl$; $R_3 = H, R_4 = -CONH_2$ | — | — |
| 3,5-Dichloro-4-(2-imidazolidinylideneamino)-benzenecarboxamide Free Base $R_1 = Cl; R_2 = H; R_3 = NH_2; R_4 = CH_3$ 6-Chloro-$N^1 = $ (2-imidazolidinylidene)-4-methyl-1,5-benzenediamine Dihydrochloride | | |

TABLE I-continued
IOP Lowering Data
(Drop In Intraocular Pressure
After Topical Administration Of Drug)

| Compound | 50% sleeptime pro. in mice tested Na Hexobarbital | hrs duration |
|---|---|---|
| $R_1 = R_2 = Cl$; $R_3 = R_4 = H$ 2,6-Dichloro-N—(2-imidazolidinylidene)-benezamine Free Base | 77 | 5-6 |
| $R_1 = R_2 = Cl$; $R_3 = H, R_4 = NH_2$ 2,6-Dichloro-$N^1$—(2-imidazolidinylidene)-1,4-benzenediamine Dihydrochloride | 1,250 | 7 7 5-6 |
| $R_1 = R_2 = Cl$; $R_3 = H, R_4 = NCOH$ N—[3,5-Dichloro-4-(2-imidazolidinylideneamino)-phenyl]-formamide Free Base | 2,300 | 7-8 |
| $R_1 = R_2 = Cl$; $R_3 = H, R_4 = NCOCH_3$ N—[3,5-Dichloro-4-(2-imidazolidinylideneamino)-phenyl]-acetamide Hydrochloride | 2,100 | 7 |
| $R_1 = R_2 = Cl$; $R_3 = H, R_4 = -OH$ 3,5-Dichloro-4-(2-imidazolidinylideneamino)-phenol Hydrochloride | 10,000 | |
| $R_1 = R_2 = Cl$; $R_3 = -NH_2, R_4 = H$ 2,6-Dichloro-$N^1$—(2-imidazolidinylidene)-1,3-benzenediamine Hydrochloride | 175 | 7 |
| $R_1 = R_2 = Cl$; $R_3 = H, R_4 = -CH_2-OH$ 3,5-Dichloro-4-(2-imidazolidinylideneamino)-benzenemethanol Hydrochloride | 1,080 | 5-6 |
| $R_1 = R_2 = Cl$; $R_3 = H, R_4 = COOH$ 3,5-Dichloro-4-(2-imidazolidinylidene amino)-benzoic Acid | 12,150 | |
| $R_1 = R_2 = Cl$; $R_3 = H, R_4 = CO_2C_2H_5$ 3,5-Dichloro-4-(2-imidazolidinylideneamino)-benzoic Acid Ethyl Ester | 4,050 | 5-6 4-5 |
| $R_1 = R_2 = Cl$; $R_3 = H, R_4 = N(CH_3)_2$ 2,6-Dichloro-$N^1$—(2-imidazolidinylidene)-$N^4,N^4$-dimethyl-1,4-benzenediamine Dihydrochloride | 2,950 | |
| $R_1 = R_2 = $ ethyl; $R_3 = H, R_4 = H$ 2,6-Diethyl-N—(2-imidazolidinylidene)-benzamine Free Base | 420 | |
| $R_1 = R_2 = $ ethyl; $R_3 = H, R_4 = NH_2$ 2,6-Diethyl-$N^1$—(2-imidazolidinylidene)-1,4-benzenediamine Dihydrochloride | 340 | |
| $R_1 = R_2 = $ ethyl; $R_3 = H, R_4 = -NCOCH_3$ N—[2,6-Diethyl-4-(2-imidazolidinylideneamino)-phenyl]-acetamide Hydrochloride | — | |
| $R_1 = R_2 = $ ethyl; $R_3 = -NH_2, R_4 = H$ 2,6-Diethyl-$N^1$—(2- | 1,100 | |

TABLE I-continued

IOP Lowering Data
(Drop In Intraocular Pressure
After Topical Administration Of Drug)

imidazolidinylidene)-
1,3-benzenediamine
Dihydrochloride
$R_1 = R_2 = Cl$;    4,050
$R_3 = H, R_4 = -CN$
4-Cyano-2,6-dichloro-
N—(2-imidazolidinylidene)-
benzamine
$R_1 = R_2 = Cl$;    4,050
$R_3 = H, R_4 = -CONH_2$
3,5-Dichloro-4-(2-
imidazolidinylideneamino)-
benzenecarboxamide Free Base
$R_1 = Cl; R_2 = H; R_3 = NH_2$;
$R_4 = CH_3$
6-Chloro-$N^1$ = (2-
imidazolidinylidene)-
4-methyl-
1,3-benzenediamine
Dihydrochloride

[1]In testing at present in the steroid rabbit model. Duration of action in the Steroid rabbit model in hours, versus control, statistically significant 95% confidence.
[2]Dose % IOP effect at 0.25% (50 uL) topical.
[3]Dose % IOP effect at 0.125% (50 uL) topical.

The data in Columns A, B, and C of TABLE I, which are expressed as a percent lowering of IOP from control values, as well as the data in Columns D, E, and F of TABLE I establish that the disclosed compounds are capable of lowering IOP at therapeutic levels which do not affect systemic blood pressure or express any overt central nervous system side effects such as sedation.

It should be understood that while certain preferred embodiments of the present invention have been illustrated and described, various modifications thereof will become apparent to those skilled in the art. Accordingly, the scope of the present invention should be defined by the appended claims and equivalents thereof.

Various features of the invention are set forth in the following claims.

What is claimed is:

1. A method for lowering intraocular pressure comprising topically applying to the eye an effective amount for lowering such intraocular pressure of a compound of the formula

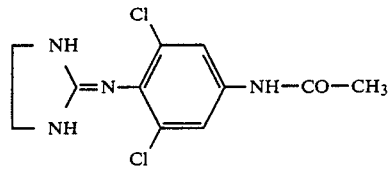

or a pharmaceutically acceptable salt thereof.

2. A method according to claim 1, which comprises applying said compound in the form of eye drops.

3. A method according to claim 2 wherein said compound comprises from about 0.10 to about 2.0 percent by weight of said eye drops.

* * * * *